United States Patent [19]

Razdan et al.

[11] 4,126,695
[45] Nov. 21, 1978

[54] ANTI-GLAUCOMA COMPOSITION AND METHOD

[75] Inventors: Raj K. Razdan, Belmont; Haldean C. Dalzell, Weston; Barbara Z. Terris, Newton; Harry G. Pars, Lexington, all of Mass.

[73] Assignee: SISA Incorporated, Cambridge, Mass.

[21] Appl. No.: 762,833

[22] Filed: Jan. 27, 1977

[51] Int. Cl.² ............................................. A61K 31/35
[52] U.S. Cl. ..................................................... 424/283
[58] Field of Search ........................................ 424/283

[56] References Cited

U.S. PATENT DOCUMENTS

| | | | |
|---|---|---|---|
| 3,668,224 | 6/1972 | Petrzilka | 424/283 |
| 3,728,360 | 4/1974 | Pars et al. | 260/345.3 |
| 3,734,930 | 5/1973 | Razdan et al. | 424/283 |
| 3,799,946 | 3/1974 | Loev | 424/283 |
| 3,920,809 | 11/1975 | Thakkar | 424/283 |
| 4,025,536 | 5/1977 | Korte et al. | 424/283 |

OTHER PUBLICATIONS

Ophthalmologica 168:366-369 (1974)-D. Shapiro The Ocular Manifestations of the Cannabinols Newsweek, Nov. 8, 1976 -Pot and Glaucoma.
Chem. Abst. 83 158,044(r) (1975)-Purnell et al. "Δ⁹-Tetrahydrocannabinol-in Man."
Chem. Abst. 84 130270(h) (1976) Green et al.-Interaction of—Tetrahydrocannabinol in the Eye."

*Primary Examiner*—Albert T. Meyers
*Assistant Examiner*—Robinson D. W.

[57] ABSTRACT

Tetrahydrodibenzopyrans having the structure

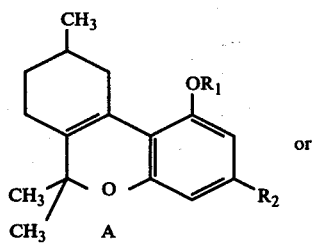

A or

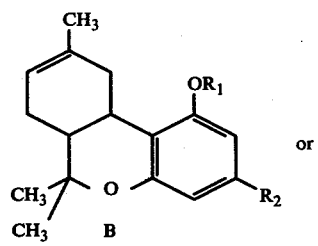

B or

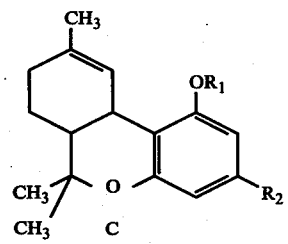

C in which $R_1$ is hydrogen or acetyl and $R_2$ is alkyl having from 1 to 4 carbon atoms are effective anti-glaucoma agents, free from all but a very small amount of CNS activity, when applied topically.

3 Claims, No Drawings

ANTI-GLAUCOMA COMPOSITION AND METHOD

This invention relates to the treatment of glaucoma, particularly wide-angle glaucoma, by topical application to the eye of a therapeutic composition consisting essentially of an ophthalmologically acceptable topical carrier and an effective amount of a compound having the structure

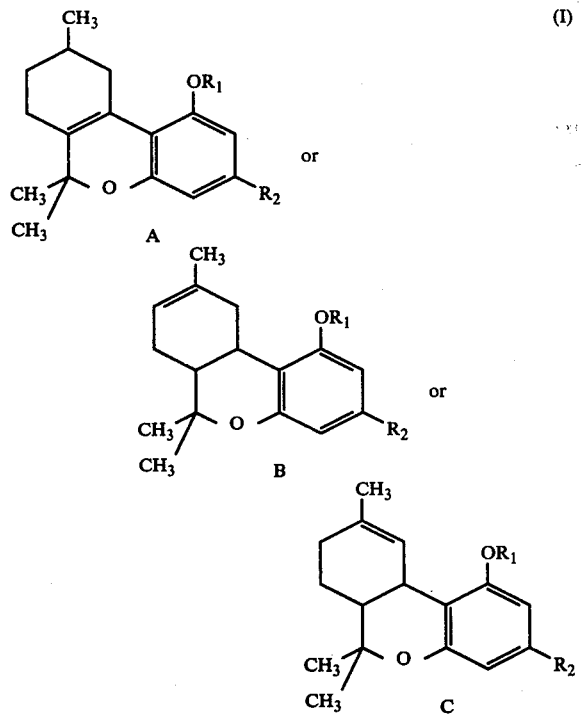

in which $R_1$ is hydrogen or acetyl and $R_2$ is alkyl having from 1 to 4 carbon atoms.

It has previously been reported that marijuana, $\Delta^9$-tetrahydrocannabinol and several benzopyranopyridines related to cannabinoids cause a fall in intraocular pressure, as stated in Pharmacology of Marijuana, Braude and Szara, (Raven, New York, 1976) pages 803–832, and in The Therapeutic Potential of Marijuana, Cohen and Stillman, (Plenum Press, New York, 1976). However, such compounds possess strong central nervous system (CNS) activity, in addition to having anti-glaucoma activity, and are therefore undesirable for use as therapeutic agents.

It has also long been known that the compounds of the present invention have very little CNS activity. Adams et al. J.A.C.S. Vol. 64, pages 694–697 (dog ataxia potency) (1942); Russell et al., J. Chem. Soc. 1941, pages 826–829 (Gayer rabbit test). Tests in mice also show the compounds to have much less CNS activity than $\Delta^9$-tetrahydrocannabinol.

It has now been found that tetrahydrodibenzopyrans having the structure defined in (I) above, although having little or no CNS activity, nevertheless possess effective anti-glaucoma activity in warm-blooded animals when applied topically to the eye. Application of the compound preferably in a suitable topical carrier to a single eye of a warm-blooded animal causes reduction of intraocular pressure in both eyes of the same animal.

The tetrahydrodibenzopyrans useful in the present invention, which are water-insoluble materials, can be prepared as described by Ghosh et al., J. Chem. Soc. 1940, pages 1121–1125 and by Adams et al., J.A.C.S. Vol. 62, pages 2405–2408 (1940) and in Petrzilka U.S. Pat. Nos. 3,560,528 and 3,668,224.

The tetrahydrodibenzopyran compounds can be formulated with conventional ophthalmologically acceptable topical carriers, preferably those for water-insoluble medicaments; such carriers may and preferably do include a compatible bacteriostat and/or antioxidant as preservatives of the formulation in storage and use. Among suitable carriers are mineral oil, petrolatum, vegetable oils such as peanut oil and sesame oil, and similar oleaginous materials. If desired, the oleaginous formulation can be dispersed in water or an aqueous medium to form an emulsion or dispersion. The preparation of such formulations is carried out under aseptic conditions to give a sterile product.

The tetrahydrodibenzopyran compounds which are the active agents can be employed in varying concentration in the carrier, from $10^{-4}\%$ to 10% or more by weight, preferably from 0.01% to 1%. The dose may also vary considerably, from 0.00003 mg. per kg. body weight to 3.3 mg/kg, preferably fromm 0.003 to 0.3 mg/kg, best results being obtained at a dosage level from 0.03 to 0.3 mg/kg.

EXAMPLES

The active agents were evaluated by topical application to the cornea of one eye of a conscious adult albino rabbit (wt. 2–4 kg) of either sex. The test formulation consisted of a solution in light mineral oil (Saybolt viscosity 125–135) containing in one case 0.1% and in another case 1.0% by weight of the active agent. One 50 microliter drop of the solution was applied to the 12 o'clock position and allowed to flow over the surface of the cornea of the right eye of each rabbit, and the intraocular pressure in both eyes in each rabbit was measured at hourly intervals after initial application using an Alcon pneumotonograph which had been calibrated for rabbit eyes. Each measurement was made after application of a drop of tetracaine hydrochloride solution (0.5%) which was washed off after 5 to 10 seconds with at least 1 ml of saline solution. Four hours after initial application of the mineral oil solution, the application was repeated.

There was employed as a control a mineral oil solution containing 0.1% by weight of $\Delta^9$-tetrahydrocannabinol. The compounds tested were 1-acetoxy-3,6,6,9-tetramethyl-7,8,9,10-tetrahydro-6H-dibenzo[b,d]pyran (I A wherein $R_1$ is acetyl and $R_2$ is methyl); and 1-hydroxy-3,6,6,9-tetramethyl-7,8,9,10-tetrahydro-6H-dibenzo[b,d]pyran (I A wherein $R_1$ is hydrogen and $R_2$ is methyl).

The results were as follows:

| Compound | Maximum Fall in Intraocular Pressure, Percent | | Time to Maximum Fall, Minutes |
|---|---|---|---|
| Control (0.1%) | RE* | 16.8 ± 1.5 | 360 |
|  | LE | 14.2 ± 1.8 | 360 |
| (IA) wherein $R_1$ is acetyl and | RE | 25.2 ± 1.5 | 180 |

-continued

| Compound | | Maximum Fall in Intraocular Pressure, Percent | Time to Maximum Fall, Minutes |
|---|---|---|---|
| $R_2$ is methyl, 0.1% | LE | 18.2 ± 1.8 | 180 |
| Same, 1.0% | RE | 21.8 ± 0.5 | 120 |
| | LE | 16.5 ± 1.7 | 180 |
| (IA) wherein $R_1$ is hydrogen and $R_2$ is methyl, 0.1% | RE | 19.1 ± 1.3 | 180 |
| | LE | 16.9 ± 1.7 | 240 (remained at max. fall for 60 min.) |
| Same, 1.0% | RE | 16.9 ± 1.6 (Decreased to 13% fall after 240 minutes, then increased to 16.9 ± 2.3 at 300 min.) | 180 |
| | LE | 13.1 ± 2.5 (Decreased to 12% fall at 180 min., then increased to 13.1 ± 1.3 at 240 min.) | 120 |

*RE = right eye; LE = left eye.

Similar results can be obtained when there are substituted as the active agents 1-hydroxy-3,6,6,9-tetramethyl-6a,7,10,10a-tetrahydro-6H-dibenzo[b,d]pyran (I B wherein $R_1$ is hydrogen and $R_2$ is methyl) and 1-hydroxy-3,6,6,9-tetramethyl-6a,7,8,10a-tetrahydro-6H-dibenzo[b,d]pyran (I C wherein $R_1$ is hydrogen and $R_2$ is methyl).

In general, the compounds of the present invention show a long duration of action, lasting from one hour to as much as 5–6 hours.

What is claimed is:

1. The method of treating wide angle glaucoma which comprises applying topically to the eye from 0.00003 to 3.3 mg/kg of body weight of a compound selected from the group consisting of those having the structure

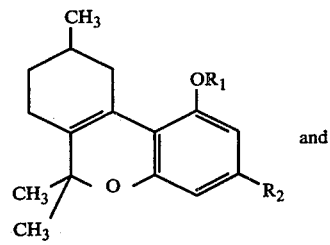

and

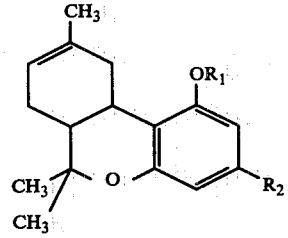

and

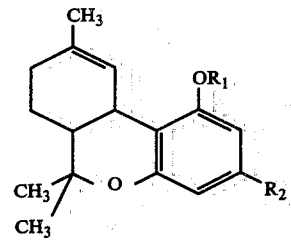

wherein $R_1$ is acetyl and $R_2$ is alkyl having 1 to 4 carbon atoms.

2. The method as claimed in claim 1 wherein the compound has the structure

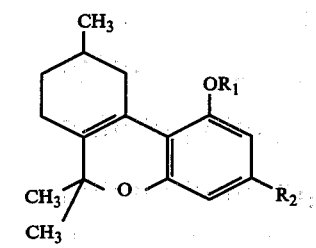

wherein $R_1$ is acetyl and $R_2$ is alkyl having 1 to 4 carbon atoms.

3. The method as claimed in claim 2 wherein $R_1$ is acetyl and $R_2$ is methyl.

UNITED STATES PATENT AND TRADEMARK OFFICE
CERTIFICATE OF CORRECTION

PATENT NO. : 4,126,695

DATED : November 21, 1978

INVENTOR(S) : Raj K. Razdan et al.

It is certified that error appears in the above—identified patent and that said Letters Patent are hereby corrected as shown below:

Under References Cited, "4/1974" should be "4/1973";

Column 1, after the formula, "(I)" should be inserted;

Column 2, line 30, "from" is misspelled.

Signed and Sealed this

Thirteenth Day of March 1979

[SEAL]

Attest:

RUTH C. MASON
Attesting Officer

DONALD W. BANNER
Commissioner of Patents and Trademarks